United States Patent
Keay et al.

(10) Patent No.: US 6,232,289 B1
(45) Date of Patent: May 15, 2001

(54) METHOD OF TREATING INTERSTITIAL CYTITIS WITH RECOMBINANT HEPARIN-BINDING EPIDERMAL GROWTH FACTOR-LIKE GROWTH FACTOR (HB-EGF)

(75) Inventors: Susan Keay, Ellicott City; John Warren, Baltimore; Michael Hise, Columbia, all of MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 09/293,037

(22) Filed: Apr. 16, 1999

Related U.S. Application Data
(60) Provisional application No. 60/082,070, filed on Apr. 17, 1998.

(51) Int. Cl.[7] .................................................... C07K 14/00

(52) U.S. Cl. ................................................ 514/2; 514/12

(58) Field of Search ............................................ 514/2, 12

(56) References Cited

U.S. PATENT DOCUMENTS 5,811,393 * 9/1998 Klagsburn et al. .
5,962,645 * 10/1999 Keay et al. ........................ 530/350

OTHER PUBLICATIONS

Bowie et al., Science 247:1306–1310, 1990.*
Wells, Biochemistry 29:8509–8517, 1990.*
Ngo et al., The Protein Folding Problem and Tertiary Structure Prediction, Merz et al., eds., Birkhauser, boston, pp. 492–495, 1994.*
Cribbs et al. "Acceleration of Partial–Thickness Burn Wound Healing with Topical Application of Heparin–Binding EGF–Like Growth Factor (HB–EGF)". *Journal of Burn Care & Rehabilitation*. Mar./Apr. 1998. pp. 95–101.
Sant et al. "Interstitial cystitis". Voiding dysfunction and female urology. 297–302. 1999 Lippincott Williams & Wilkins.
Erickson et al. "Interstitial Cystitis". *Int. Urogynecol.J* (1998) 9:174–183.
Hanno, P.M., et al. eds. *Interstitial cystitis*. London: Springer–Verlag (1990).
Held, P.J. et al. "Epidemiology of interstitial cystitis: 2." *Interstitial cystitis.*: 29–48. London: Springer–Verlag (1990).
Johansson, S.L. et al. "Clinical feature and spectrum of light microscopic changes in interstitial cystitis." J. Urol, 143: 118 (1990).
Oravisto, K.J. et al. "Interstitial cystitis: Clinical and immunological findings." Scand. J. Urol. Nephrol. 4:37 (1970).
Skoluda, et al. "Kritische Bemerkungen zur Immunopathogenese der Interstitiellen Cystitis." Urologe, 13: 15 (1974).
Parsons, et al. "Epithelial dysfunction in nonbacterial cystitis (interstitial cystitis)." J. Urol 145:732 (1991).

Smith, B.H. et al. "Chronic ulcerating interstitial cystitis (Hunner's ulcer)." Arch. Path. 93:76 (1972).
Fowler J. Jr., et al. "Interstitial cystitis is associated with intraurothelial Tamm–Horsfall protein." J. Urol. 104: 1385 (1988).
Liebert, M., et al. "Evidence for urothelial cell activation in interstitial cystitis." J. Urol. 149: 470 (1993).
deBoer, W.I., et al. "Expression of growth factors and receptors during specific phases in regenerating urothelium after acute injury in vivo." Am. J. Pathol. 145: 1199 (1994).
Lynch, S.E., et al. "Growth factors in wound healing. Single and synergistic effects on partial thickness porcine wounds." J. Clin. Invest. 84: 640 (1989).
Mustoe, T.A., et al. "Growth factor–induced acceleration of tissue repair through direct and inductive activities in a rabbit dermal ulcer model." J. Clin. Invest. 87: 694 (1991).
Mellin, T.N., et al. "Acidic fibroblast growth factor accelerates dermal wound healing." Growth Factors 7: 1 (1992).
Antoniades, H.N., et al. "Expression of growth factor and receptor mRNAs in skin epithelial cells following acute cutaneous injury." Am. J. Pathol. 142: 1099 (1993).
Werner, S., et al. "Large induction of keratinocyte growth factor expression in the dermis during wound healing." Proc. Natl. Acad. Sci. USA 89: 6896 (1992).
Nusrat, A., et al. "Hepatocyte growth factor/scatter factor effects on epithelia." J. Clin. Invest. 93: 2056 (1994).

(List continued on next page.)

*Primary Examiner*—Elizabeth C. Kemmerer
(74) *Attorney, Agent, or Firm*—Steven J. Hultquist; William A. Barrett

(57) ABSTRACT

Interstitial cystitis (IC) is a chronic bladder disease for which the exact etiology is unknown and for which there is no reliably effective treatment. However, it is known that the bladder epithelium is often abnormal in IC. We discovered that human bladder epithelial cells from both normal controls and IC patients are inhibited from proliferating by an anti-proliferative factor (APF) present in IC urine specimens. Inhibited proliferation may cause epithelial abnormalities characteristic of IC such as ulcerations and multiple tears in the bladder epithelium. We further discovered that 1) levels of heparin binding-epidermal growth factor-like growth factor (HB-EGF), a factor known be important for epithelial cell proliferation and wound healing in other tissues, are abnormally low in the urine of patients suffering from IC as compared to asymptomatic controls or patients with acute bacterial cystitis; 2) the APF found in IC urine specimens inhibits HB-EGF production by bladder epithelial cells; and 3) that the administration of rHB-EGF blocks the effects of APF on bladder epithelial cells from either IC patients or controls. The invention herein is directed to the administration of HB-EGF, or a functional derivative or agonist thereof, to bladder epithelial cells to inhibit the effects of APF on bladder cell proliferation, thereby reducing or eliminating the chronic damage to the bladder epithelium. HB-EGF or a functional derivative may be used as a therapy for patients suffering from IC or other diseases characterized by inhibited epithelial cell proliferation.

23 Claims, 11 Drawing Sheets

OTHER PUBLICATIONS

Behrens, M.T., et al. "Epidermal growth factor receptor regulation in rat kidney: two models of renal growth." Am. J. Physiol. 257: F1059 (1989).

McCarthy, D.W., et al. "Production of heparin–binding epidermal growth factor–like growth factor (HB–EGF) at sites of thermal injury in pediatric patients." J. Invest. Dermatol. 106: 49 (1996).

Marikovsky, M., et al. "Appearance of heparin–binding EGF–like growth factor in wound fluid as a response to injury." Proc. Natl. Acad. Sci USA 90: 3889 (1993).

Homma, T., et al. "Induction of heparin–binding epidermal growth factor–like growth factor mRNA in rat kidney after acute injury." J. Clin. Invest. 96: 1018 (1995).

deBoer, W.I., et al. "Characterization of distinct functions for growth factors in murine transitional epithelial cells in primary organotypic culture." Exp. Cell Res. 214: 510 (1994).

Jorgensen, P.E., et al. "Urinary epidermal growth factor is excreted from the rat isolated perfused kidney in the absence of plasma." J. Endocrinol. 139: 227 (1993).

Southgate, J., et al. "Normal human urothelial cells in vitro: proliferation and induction of stratification." Lab. Invest. 71: 583 (1994).

Chin, E. et al. "Insulin–like growth factor system gene expression in the human kidney." J. Cin. Endocrinol. Metab. 75: 962 (1992).

Jones, J. I., et al. "Insulin–like growth factors and their binding proteins: biological actions." Endocrine Rev. 16: 3 (1995).

Freeman, M.R., et al. "Human urothelial cells secrete and are regulated by heparin–binding epidermal growth factor–like growth factor (HB–EGF)." Proc. Am. Urol. Assoc. 153: 316A (1995).

Tobin, M.S., et al. "Growth factor biology of human urothelial cells grown under serum–free conditions." Proc. Am. Urol Assoc. 153; 406A (1995).

Division of Kidney, Urolog, and Hematologic Diseases (DKUHD) of the National Institute of Diabetes and Digestive and Kidney Diseases (NIDDK). "Diagnostic criteria for research studies (interstitial cystitis)." Am. J. Kidney Dis. 13: 353 (1989).

Third Symposium on Insulin–like Growth Factors. "Valid measurements of total IGF concentrations in biological fluids." Endocrinology 136: 816 (1995).

Schirmeister, J., et al. "Plasmakreatinin alf grober indikator der nierenfunktion." Dtsch. Med. Wschr. 89: 1018 (1964).

Shishido, Y., et al. "Heparin–like molecules on the cell surface potentiate binding of diphtheria toxin to the diphtheria toxin receptor/membrane–anchored heparin–binding epidermal growth factor–like growth factor." J. Biol. Chem. 271: 29578 (1995).

Dreyer, M., et al. "Prolonged Plasma Half–Life of Insulin in Patients with a Genetic Defect of High Affinity Binding Sites", *Horm. Metabol. Res.* 18 (1986) 247–249.

Quattrin, T., et al. "Comparison of Urinary Growth Hormone and IGF–I Excretion in Small– and Appropriate–for–Gestational–Age Infants and Healthy Children[1]". *Pediatric Research*. vol.28, No. 3, 1990.

Keay, S., et al. "A Prospective Study of Microorganisms in Urine and Bladder Biopsies from Interstitial Cystitis Patients and Controls". *Urology*. Feb. 1995. vol. 45, No. 2.

Moxham C., et al. "Insulin action impaired by deficiency of the G–protein subunit $G_{i\alpha2}$". *Nature*. vol. 379. Feb. 29, 1996.

Göran L. Matejka et al. "IGF–I Binding and IGF–I mRNA expression in the post–ischemic regenerating rat kidney" Kidney Int'l 42:1113–1123 (1992).

Keay et al. "Decreased $^3$H–Thymidine Incorporation by Human Bladder Epithelial Cells Following Exposure to Urine From Interstitial Cystitis Patients" J. Urol. 156(6):2073–2078 (1996).

Burgess, W.H. et al. "Possible Dissociation of the Heparin–binding and Mitogenic Activities of Heparin–binding (Acidic Fibroblast) Growth Factor–1 from Its Receptor–binding Activities by Site–directed Mutagenesis of a Single Lysine Residue". *J. Cell Biology*. vol. 111. Nov. 1990. 2129–2138.

Lazar, E., et al. "Transforming Growth Factor α: Mutation of Aspartic Acid 47 and Leucin 48 Results in Different Biological Activities". *Molecular and Cellular Biology*. Mar. 1988. 1247–1252.

Tao, Mi–Hua, et al. "Role of Carbohydrate in the Structure and Effector Functions Mediated by the Human IgG Constant Region[1]". *Journal of Immunology*. vol. 143. 2595–2601. No. 8. Oct. 15, 1989.

* cited by examiner

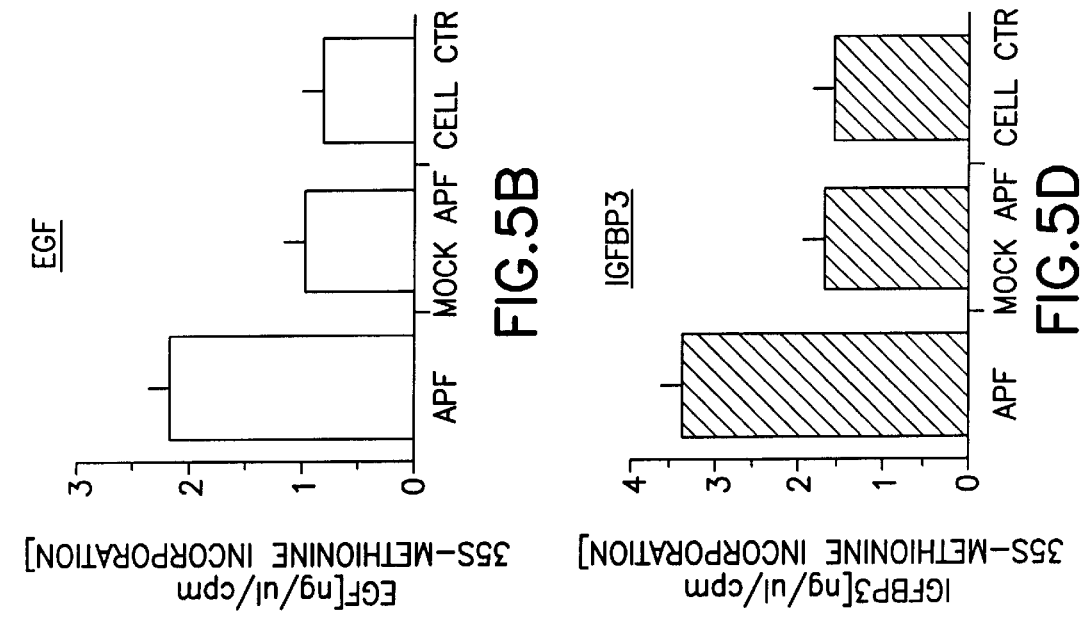
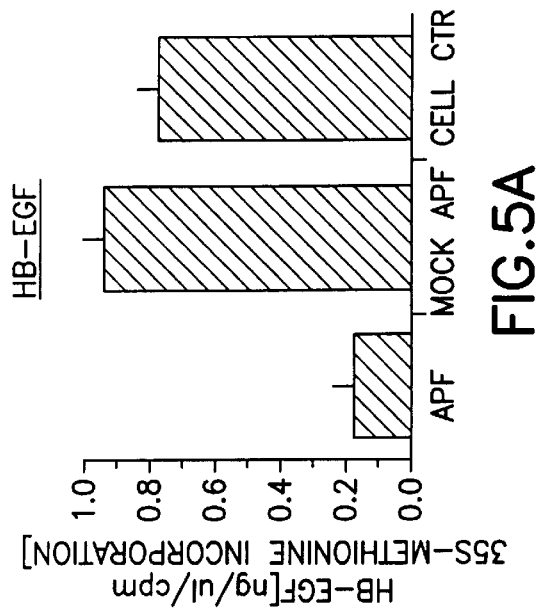
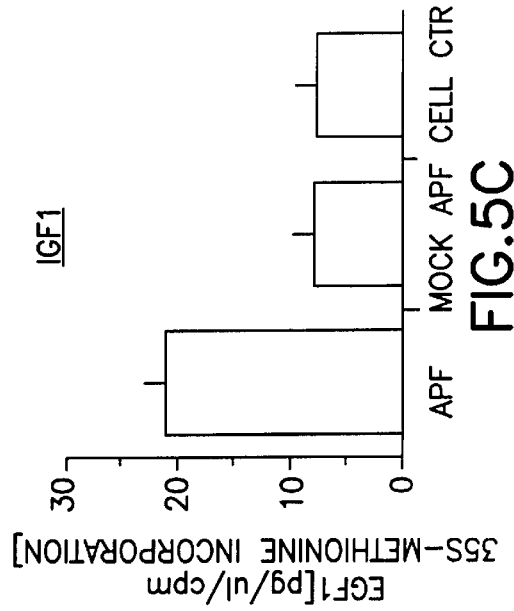

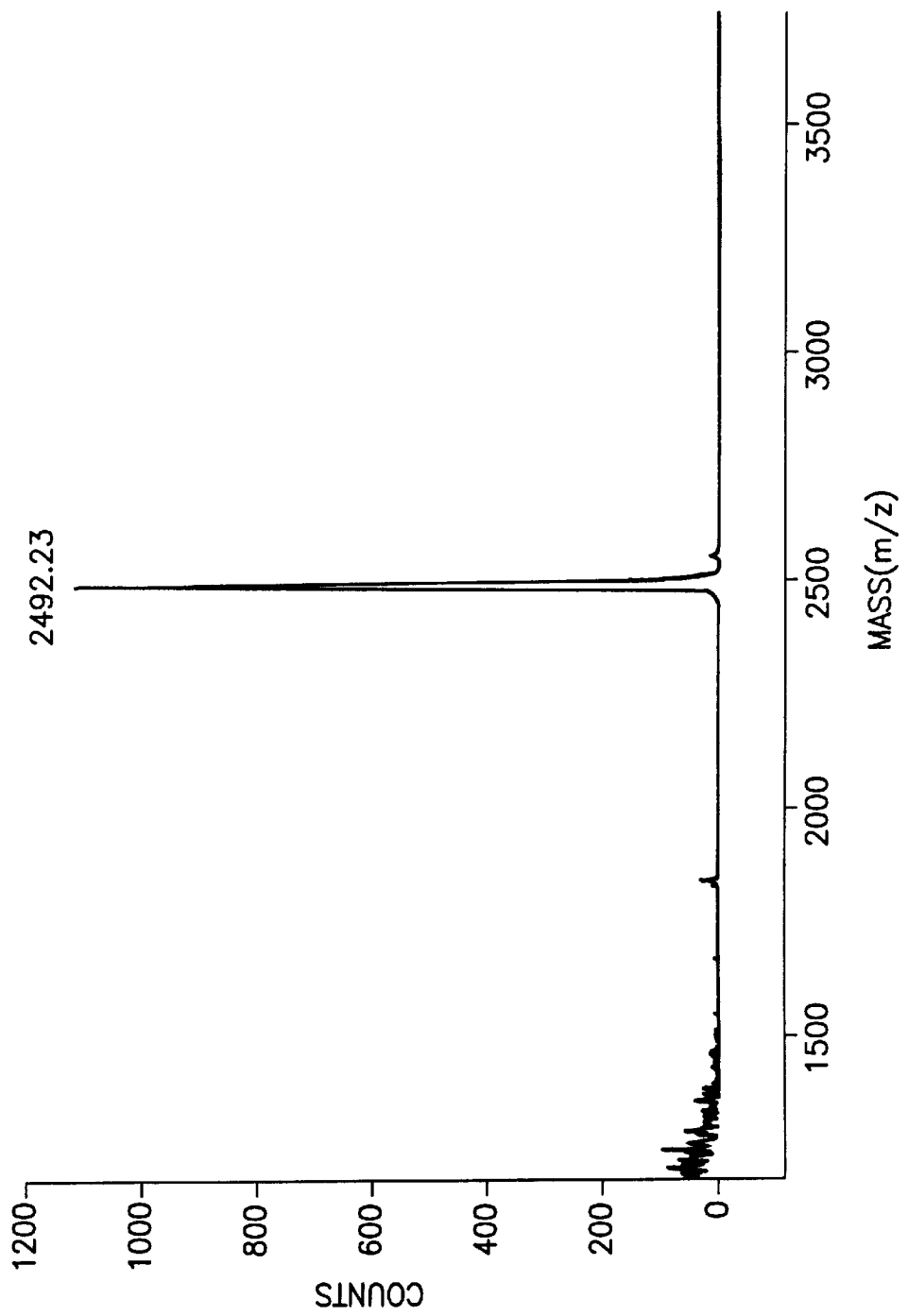

METHOD OF TREATING INTERSTITIAL CYTITIS WITH RECOMBINANT HEPARIN-BINDING EPIDERMAL GROWTH FACTOR-LIKE GROWTH FACTOR (HB-EGF)

CROSS-REFERENCE TO RELATED APPLICATIONS

This application claims priority to provisional application 60/082,070 filed Apr. 17, 1998. In addition, this application is related to co-pending provisional U.S. patent application Ser. No. 60/051,458, filed Jun. 30, 1997, entitled "Concentrations of Heparin Binding-Epidermal Growth Factor in the Urine of Interstitial Cystitis Patients and Controls" and to non-provisional U.S. patent application Ser. No. 08/944,202, filed Oct. 3, 1997, entitled "A Novel Anti-proliferative Factor from Patients with Interstitial Cystitis", now U.S. Pat. No. 5,962,645.

SPONSORSHIP

The development of the present invention was supported by the University of Maryland, Baltimore, Md., the Fishbein Foundation, and the Interstitial Cystitis Association.

FIELD OF THE INVENTION

The field of this invention generally relates to the treatment of diseases characterized by bladder epithelial abnormalities using heparin-binding epidermal growth factor-like growth factor (HB-EGF) or a functional derivative thereof to stimulate epithelial cell proliferation. The field of this invention specifically relates to the treatment of Interstitial Cystitis (IC) using recombinant HB-EGF to overcome the inhibition of bladder epithehial cell proliferation caused by a low molecular weight anti-proliferative factor found in the urine of IC patients.

BACKGROUND OF THE INVENTION

Interstitial cystitis (IC) is a chronic inflammatory disease of the bladder for which the etiology is unknown. IC often has a rapid onset with pain, urgency and frequency of urination, and cystoscopic abnormalities including petechial hemorrhages (glomerulations) or ulcers that extend into the lamina propria (Hunner's ulcers)[1,2]. The rapid onset of IC is followed by a chronic course with partial remissions and re-exacerbations, which can continue for up to 30 years[1,2]. As a result of the absence of a specific cause for and lack of understanding of its pathogenesis, there is currently no generally accepted treatment proven to be reliably efficacious.

Various groups have studied IC and speculated as to its cause. Proposed etiologies include infection, allergic or immune disorders, endocrinologic disturbance, toxic urinary chemicals, defective transitional mucosa, psychiatric disorders, neurogenic disorders, lymphatic obstruction, vascular obstruction. Proposed treatments include pentosan polysulfate, anti-inflammatory or immunosuppressant therapy, muscle relaxants, anti-histamines, and analgesics. Of these, only pentosan polysulfate has been approved by the FDA. However, none of the proposed therapies, including pentosan polysulfate, is universally accepted or universally efficacious. As a result, there is a long felt need for adequate therapy of this misunderstood and frequently misdiagnosed disorder.

Certain morphologic and histologic features of IC suggest that the epithelium is usually abnormal in this disease[3-5], with evidence for changes in the bladder mucin layer[6], denudation or thinning of the bladder epithelium and rupture of the mucosa[3-5,7], and intraurothelial infiltration of urinary proteins such as Tamm-Horsfall protein[8]. In addition, activation of bladder epithelial cells appears to be abnormal in IC, with altered expression of specific cellular proteins[9]. These changes coupled with the chronic nature of IC suggests the possibility of impaired regeneration of normal bladder epithelium. In previous experiments, we discovered a 1–3 kDa peptide in the urine of IC patients that inhibits the proliferation of cultured normal adult human bladder epithelial cells, suggesting that it may be related to the pathogenesis of this disorder (see co-pending application Ser. No. 08/944,202). This peptide is hereafter referred to as the anti-proliferative factor or APF.

The uninjured postnatal urothelium regenerates very slowly, but rapid proliferation of uroepithelial cells in vivo can occur during tissue regeneration in response to injury[10]. The limited data that exist for bladder epithelial cells suggest their replication and differentiation are probably influenced by specific paracrine or autocrine growth factors and their regulatory proteins, similar to other types of epithelial cells[10-21]. Epithelial cell growth factors known to be present in normal human urine include epidermal growth factor (EGF), insulin-like growth factors (IGF's), insulin-like growth factor binding proteins (IGFBP's), heparin-binding epidermal growth factor-like growth factor (HB-EGF), platelet-derived growth factors (PDGF-A and B), fibroblast growth factors (FGF1 and 2), and transforming growth factor beta (TGFβ). EGF, which is produced primarily by cells in the thick ascending limb of Henle and the distal convoluted tubule[22], is present in high concentrations in urine, and can stimulate, but is not required for, mouse bladder epithelial cell proliferation in vitro[23]. IGF1 and IGF2 are produced by both kidney and bladder cells and appear to be required for bladder epithelial cell proliferation[10,21,24]. The major IGFBP's found in human urine, which can regulate the activity of IGF1 and 2, are IGFBP-2 and IGFBP-3[25]. HB-EGF is also known to be produced by human bladder epithelial cells and can stimulate their growth in vitro[26,27]. In contrast, current data suggest that the PDGF's, FGF's and TGFβ affect bladder epithelial cell migration and/or differentiation, but their role in cell proliferation remains uncertain[10,21].

Exogenously applied growth factors can stimulate epithelial wound repair[11-13]. Since IC is histologically characterized by epithelial abnormalities and because the mucosal defects present in IC result in exposure of basal undifferentiated cells and their growth factor receptors to urine growth factors, we reasoned that abnormally low levels of urinary growth factors, such as HB-EGF, that stimulate bladder epithelial cell proliferation could adversely affect bladder epithelial wound repair and be part of the etiology of IC.

We measured urinary levels of HB-EGF in women with IC, asymptomatic control women without bladder disease, and women with acute, self-limited bladder epithelial damage from bacterial cystitis. We discovered that urine levels of HB-EGF are specifically and significantly decreased in the urine of IC patients (see co-pending application Ser. No. 60/051,458). Furthermore, recent data indicate that 1) IC urine contains a low molecular weight anti-proliferative factor (APF) that specifically inhibits HB-EGF production by primary human bladder epithelial cells in vitro and 2) the inhibition of bladder epithelial cell proliferation caused by the APF from IC urine specimens can be blocked by the addition of recombinant HB-EGF to the cell medium.

Based on the above, we have concluded that 1) a low molecular weight factor from IC urine (APF) inhibits HB-EGF production by bladder epithelial cells and 2) HB-EGF may be used as a therapeutic to stimulate bladder epithelial cell proliferation in the presence of the APF, thereby effectively treating IC.

SUMMARY OF THE INVENTION

It is the object of the invention to provide a reliably effective therapy for diseases associated with inhibited epithelial cell proliferation, particularly bladder epithelial cell proliferation, more particularly interstitial cystitis (IC), using heparin-binding epidermal growth factor-like growth factor (HB-EGF) which is capable of inhibiting the antiproliferative activity present in most IC urine specimens or an analogue, variant, or derivative thereof having the same functional activity and capability.

It is a further object of the invention to administer HB-EGF or agents that stimulate HB-EGF production or mimic its activity to injured epithelial cells in a form suitable to provide the desired inhibition of anti-proliferation or stimulation of cell replication. The form may be suitable for exogenous or endogenous application. The form may be suitable for local or topical application, such as a liquid, a cream, an ointment, a suppository, or a gel that may be superficially applied to the tissues. Alternatively, the form may be suitable for systemic administration, such as oral or parenteral formulations. The administration may be in the form of discrete doses or in a form capable of continuous delivery.

It is a further object of the invention to administer an agonist of HB-EGF or agents that increase the efficacy of HB-EGF in a subject. As described in detail herein, an agonist of HB-EGF is any compound which is capable of increasing the efficacy of a function of HB-EGF and includes, for example, agents which promote the synthesis of HB-EGF by the subject, etc.

It is a further object of the invention to administer anti-idiotypic antibodies, or analogues of HB-EGF, or agents which mimic HB-EGF activity, or a combination of any of the above can be provided to a subject in need of such treatment.

BRIEF DESCRIPTION OF THE DRAWINGS

FIGS. 5A–5D: Depicts the production of specific growth factors [HB-EGF, EGF, IGF1, and IGFBP3] by human bladder epithelial cells in vitro in response to HPLC purified APF.

FIG. 7A depicts the inhibition of $^3$H-thymidine incorporation (denoted as percent inhibition), a measure which correlates to the inhibition of cell proliferation, into normal adult human bladder epithelial cells incubated in IC urine specimens, serum free cell culture medium alone, bacterial cystitis (BC) urine specimens, or vulvovaginitis (VV) urine specimens. FIG. 7B depicts the inhibition of $^3$H-thymidine incorporation (denoted as percent change of $^3$H-thyrnidine incorporation), a measure which correlates to the inhibition of cell proliferation, into normal adult human bladder epithelial cells incubated in IC patient bladder urine specimens or IC patient renal pelvic urine specimens.

FIG. 8: Depicts the mass spectrometric analysis of HPLC-purified APF.

DETAILED DESCRIPTION OF THE INVENTION

Figure 1A:
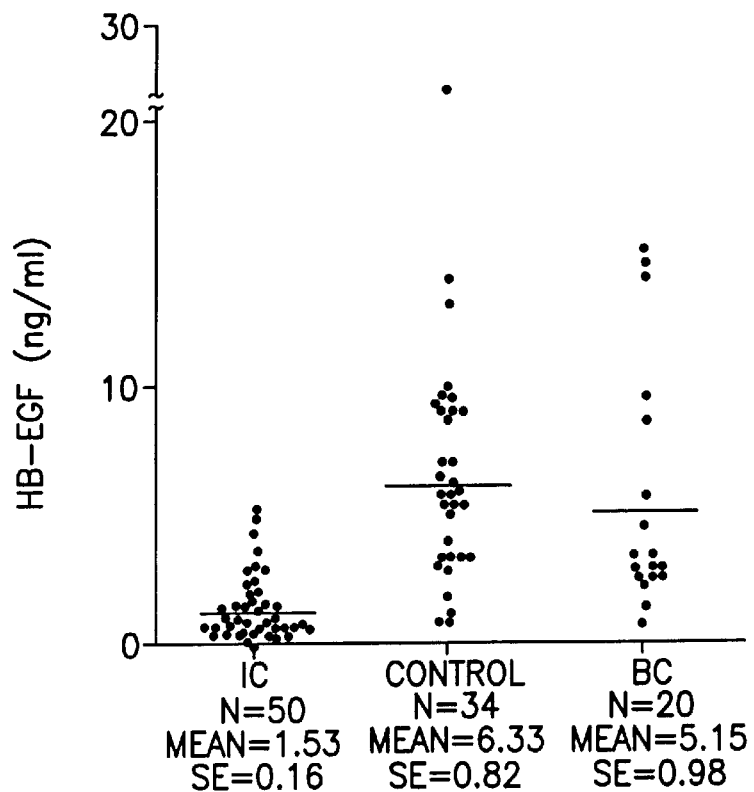
FIGS. 1A–1B: Depicts concentrations of HB-EGF in urine specimens from women with IC, asymptomatic control women without bladder disease, and women with acute, self-limited bladder epithelial damage from bacterial cystitis.

Interstitial cystitis (IC) is a chronic bladder disease for which the etiology is unknown and for which there is no effective and reliable therapy. The bladder epithelium is often abnormal in IC. Therefore, we reasoned that the levels of epithelial growth factors such as heparin-binding epidermal growth factor-like growth factor (HB-EGF) might be important for bladder epithelial proliferation. ELISAs were used to determine levels of heparin binding epidermal growth factor-like growth factor (HB-EGF) as well as other growth factors in urine specimens from women with IC, asymptomatic control women without bladder disease, and women with acute, self-limited bladder epithelial damage from bacterial cystitis. The levels of the other growth factors assayed in urine from IC patients proved to be slightly elevated when compared to urine from normal and bacterial cystitis controls (See FIGS. 2–4). However, urine HB-EGF levels were specifically and significantly decreased in IC patients as compared to asymptomatic controls or patients with bacterial cystitis, whether expressed as concentration (amount per volume of urine) or the amount relative to urine creatinine in each specimen (See FIG. 1). These findings indicate that complex changes in the levels of urine growth factors are associated with IC, including significant and specific decreases in HB-EGF levels in the urine of IC patients (see co-pending application Ser. No. 60/051,458).

Human bladder epithelial cells are known to produce HB-EGF[26]. Inhibition of their proliferation in vitro in the presence of IC urine and under conditions of serum starvation may therefore be related to a dysregulation of HB-EGF production caused by a factor in IC urine. Our experimental data shows that the in vitro production of HB-EGF by bladder epithelial cells is specifically decreased in the presence of HPLC-purified the low molecular weight (<3 kDa) fraction from IC patient urine, that fraction containing the APF, which is known to inhibit bladder cell proliferation, whereas production of other growth factors such as EGF, IGF1, and a growth factor binding protein (IGFBP3) is increased. These findings indicate that bladder epithelial cell synthesis or catabolism of specific autocrine growth factors is be regulated by the APF. Likewise, it is conceivable that the anti-proliferative effect of IC urine specimens on bladder epithelial cells could be blocked or inhibited by the addition of recombinant HB-EGP or its agonists to the cell medium.

With the above information in hand, we proceeded to assay the ability of HB-EGF to block the anti-proliferative activity of IC urine. The data herein indicate that the inhibition of bladder epithelial cell proliferation caused by the APF from IC urine specimens can be blocked by the addition of recombinant HB-EGF to the cell medium. HB-EGF appears to act as an antagonist for the APF. Therefore, our data suggest that it may be used as an effective therapeutic for the treatment of IC.

Part I. Determining Levels of HB-EGF in IC Patient and Control Specimens

A. Materials and Methods

Patients:

IC patients were referred by physicians, the National Institute of Diabetes and Digestive and Kidney Diseases (NIDDK), and the Interstitial Cystitis Association. All IC patients had previously undergone diagnostic cystoscopy, and fulfilled the NIDDK diagnostic criteria for IC[28]. For preliminary studies performed at the University of Maryland School of Medicine, urine was collected from the IC patients at least three months following the most recent know bacterial urinary tract infection and one month following the last antibiotic use. Age-, race-, and sex-matched controls were volunteers with no history of IC or other urological disease. Each control patient was required to have no symptom of urinary tract infection or antibiotic use for the last month. Urine specimens collected at the University of Pennsylvania for additional studies were obtained during routine office visits for management of IC. Patients with acute bacterial cystitis were identified at the University of Maryland School of Medicine and the University of Maryland-College Park by the presence of bacteriuria ($>10^3$ bacteria/ml with single type of bacterium isolated) plus pyuria in combination with appropriate symptoms. Twelve (12) of the fifteen (15) patients has $>10^5$ bacteria/ml. All participants were at least 18 years old and enrolled in accordance with guidelines of the Institutional Review Boards at the University of Maryland School of Medicine, the University of Maryland, College Park, and the University of Pennsylvania.

Urine and Serum Specimens:

Urine was collected by the clean catch method in which each patient wiped the labial area with 10% povidone iodine/titratable iodine 1% solution [Clinidine, Guilford, Conn.], then collected a midstream urine into a sterile container. Specimens obtained at the University of Maryland for preliminary studies (IC patients; age-, race-, and sex-matched controls; and bacterial cystitis patients) were initially kept at 4 degrees C., then transported to the laboratory where cellular debris was removed by the low speed centrifugation at 4 degrees C. Specimens obtained at the University of Pennsylvania (from IC patients only) and the University of Maryland, College Park (from bacterial cystitis patients only) for confirmatory studies were frozen at −20 degrees C. for up to 4 weeks, then transported to the University of Maryland School of Medicine on ice. Blood specimens were obtained from patients at the University of Maryland in standard vacutainer tubes and allowed to clot at room temperature prior to removal of serum. All specimens were subsequently aliquoted under sterile conditions. Urine was and stored at −80 degrees C. and serum was stored at −20 degrees C. until used.

ELISAs:

1) HB-EGF (FIGS. 1A, 1B and 11A):

To assay for the levels of HB-EGF in clinical specimens, each well of a 96 well Immulon II plate (Dynatech Laboratories, Chantilly, Va.) was coated with 200 λ urine or serum at 4 degrees C. overnight. Following 5 washes with phosphate buffer the plates were blocked with 5% fetal bovine serum/1 mM EDTA/0.05% Tween 20 in PBS. Anti-HB-EGF antibody (1 µg/ml) (R & D Systems, Minneapolis, Minn.) was added and the plates were incubated for 2 hours at 37 degrees C. Following an additional 5 washes, biotinylated anti-goat IgG/avidin D horseradish peroxidase was added and plates were incubated for 1.5 hours at room temperature, washed, and developed with ABTS [2,2'-Azino-bis-(3-ethylbenzothiazoline-6-sulfonic)] substrate. Absorbance was read at 405 nm.

2) EGF (FIGS. 2A, 2B, and 11B):

For determination of EGF levels, urine or serum from IC patients and controls was diluted 1:200–1:300 in RD5E diluent and pipetted into wells precoated with monoclonal anti-EGF antibody, according to the manufacturer's instructions (R & D Systems, Minneapolis, Minn.). Following incubation at room temperature for 4 hours, plates were washed with phosphate buffered saline (PBS) and incubated further with HRP-linked polyclonal anti-EGF, washed, and developed with tetramethylbenzidine (TMB) substrate; development was stopped with 0.2 M $H_2SO_4$.

3) IGF1 (FIGS. 3A and 3B):

Total IGF1 levels were also measured by ELISA (Diagnostic Systems Laboratories, Webster, Tex.). Urine for these determinations was concentrated 30-fold by lyophilization and reconstitution in ethanolic HCl in accordance with published recommendations[29]. After 30 minutes incubation at room temperature, samples were centrifuged at 10,000 rpm for 3 minutes to remove insoluble material, and supernatant neutralized to pH 7 with neutralization buffer. Neutralized, extracted samples were added to wells along with anti-IGF HRP-conjugate, and plates were incubated for 2 hours at room temperature. Following washes, plates were developed with TMB chromogen solution; development was stopped with 0.2 M $H_2SO_4$.

4) IGFBP3 (FIGS. 4A and 4B):

For determination of IGFBP3 levels, undiluted urine specimens were added to wells precoated with polyclonal anti-IGFBP3, then incubated at room temperature for 2 hours. Following washes, another polyclonal, HRP-labeled anti-IGFBP3 antibody was added to the wells, and the plates were further incubated, washed, and developed with TMB substrate; development was stopped with 0.2 M $H_2SO_4$.

For each protein measured, linear absorbance vs. concentration curves were prepared from results with known standard concentrations of recombinant growth factor or growth factor binding protein, and urine sample EGF, IGF1, IGFBP3 and HB-EGF concentrations were plotted. (See FIGS. 1–4).

Measurement of Urinary Creatinine:

Urinary creatinine was measured by the Jaffe method, using picric acid, as previously described[30]. Data were then expressed as both the amount of each growth factor or binding protein present per volume of urine or per milligram of urine creatinine. The latter allows the values to be normalized to kidney function (excretion rate), thereby eliminating variables due to volume produced (excretion volume).

Statistical Analysis:

For the preliminary studies, comparisons of mean difference in HB-EGF levels in urine specimens from IC patients vs. age-, race- and sex-matched controls were performed using a two-way analysis of variance, with age and case-control status as the two factors. For the confirmatory studies with larger sample populations of women with IC, asymptomatic control women, and women with bacterial cystitis, comparisons of mean difference in growth factor levels were performed using a two-tailed analysis of covariance with age as the covariate.

Logistic regression analysis was performed with case or control status serving as the dependent variable and the amount of HB-EGF serving as the independent variable. Both HB-EGF concentration per milliliter of urine and HB-EGF concentration per mg of urine creatinine were analyzed. Sensitivity and specificity were derived from the logistic regression model, and the sensitivity and specificity determined for various cutoff values.

B. Results

Figure 1B:
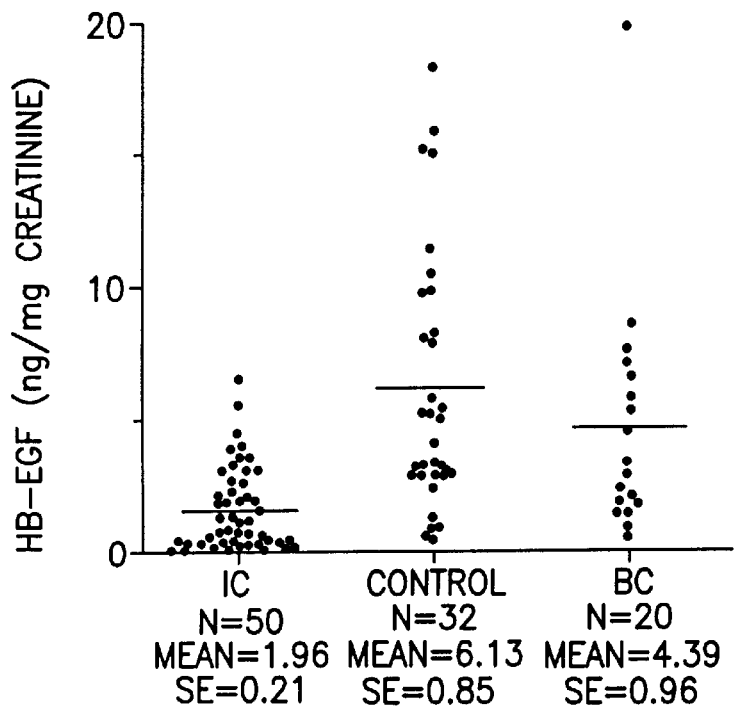

We determined the levels of HB-EGF in urine specimens from women with IC, asymptomatic control women, and women with bacterial cystitis. The quantity of immunoreactive HB-EGF in the urine of IC patients was markedly decreased as compared to asymptomatic controls, reaching significance at the level of $p<0.001$ in both the preliminary analysis (in which age-, race- and sex-matched asymptomatic controls were used) and the subsequent larger analysis (in which women with IC, asymptomatic women, and women with bacterial cystitis were studied). As shown in FIG. 1A, the concentration of HB-EGF was strikingly lower in IC patient specimens ($1.53\pm0.16$ ng/ml) as compared to asymptomatic controls ($6.33\pm0.82$ ng/ml, $p<0.001$) or patients with bacterial cystitis ($5.15\pm0.98$ ng/ml $p<0.001$), with 37 of 50 IC patients (74%) having levels below 2 ng/ml. The levels of HB-EGF were also significantly lower in IC specimens than in urine from either control group when data were expressed per milligram of urine creatinine ($p<0.001$ and $p=0.028$, respectively) (FIG. 1B).

Using the logistic regression analysis, a sensitivity of 84% and a specificity of 82% were achievable at a cutoff value of 2.9 ng HB-EGF per ml urine. (A similar analysis of ng HB-EGF per mg urine creatinine indicated lower achievable sensitivity of 72% with a specificity of 75%). If a cutoff value of 5.0 ng HB-EGF per ml urine were used, 98% sensitivity is achievable with a specificity of 59%. These findings indicate that measuring the concentration of urine HB-EGF per ml urine is useful for the diagnosis of IC, either as a single assay with a cutoff of 2.9 ng/ml or as a screening assay with a cutoff of 5.0 ng/ml.

Figure 2A:
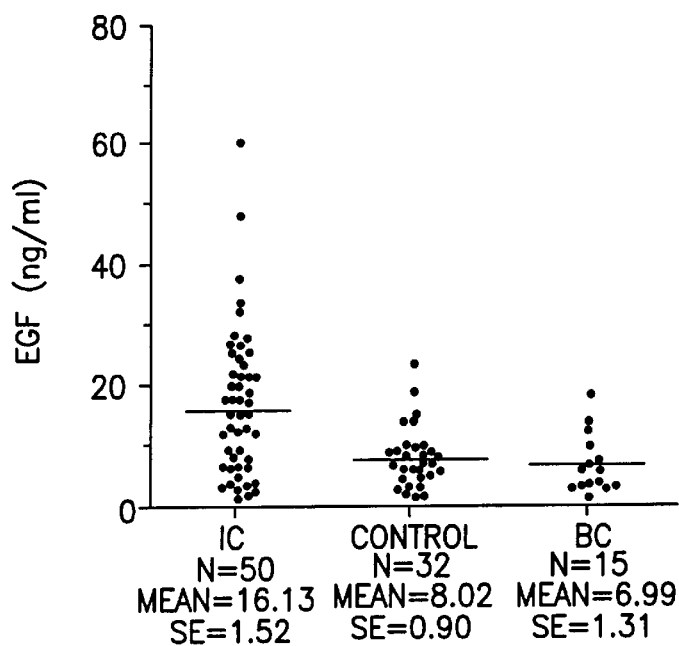
FIGS. 2A–2B: Depicts concentrations of EGF in urine specimens from women with IC, asymptomatic control women without bladder disease, and women with acute, self-limited bladder epithelial damage from bacterial cystitis.
Figure 2B:
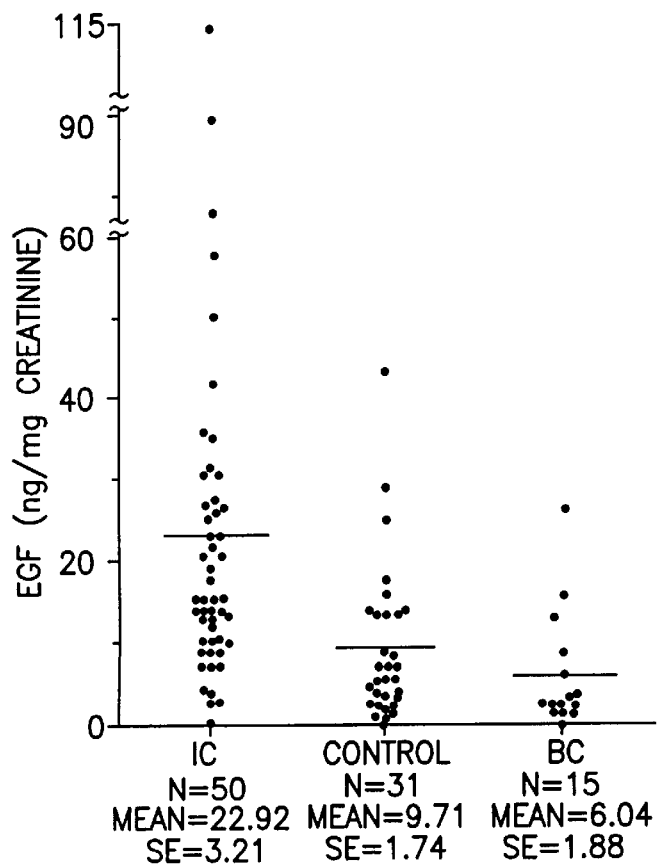

With respect to the data shown in FIG. 2, studies indicated a trend toward higher mean concentrations of immunoreactive EGF in IC specimens ($16.13\pm1.52$ ng/ml) as compared to asymptomatic controls ($8.02\pm0.90$ ng/ml) or patients with bacterial cystitis ($6.99\pm1.31$ ng/ml) ($p<0.001$ for both comparisons ) (See FIG. 2A). Similar results were obtained when the amount of EGF was expressed per milligram of urine creatinine ($p=0.001$ for a comparison of IC and bacterial cystitis patients) (see FIG. 2B).

Figure 3A:
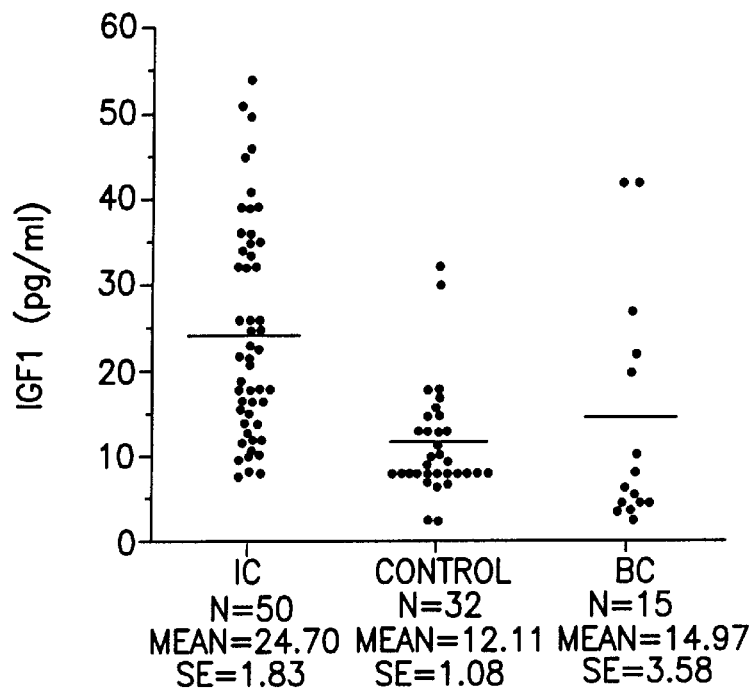
FIGS. 3A–3B: Depicts concentrations of IGF-1 in urine specimens from women with IC, asymptomatic control women without bladder disease, and women with acute, self-limited bladder epithelial damage from bacterial cystitis.
Figure 3B:
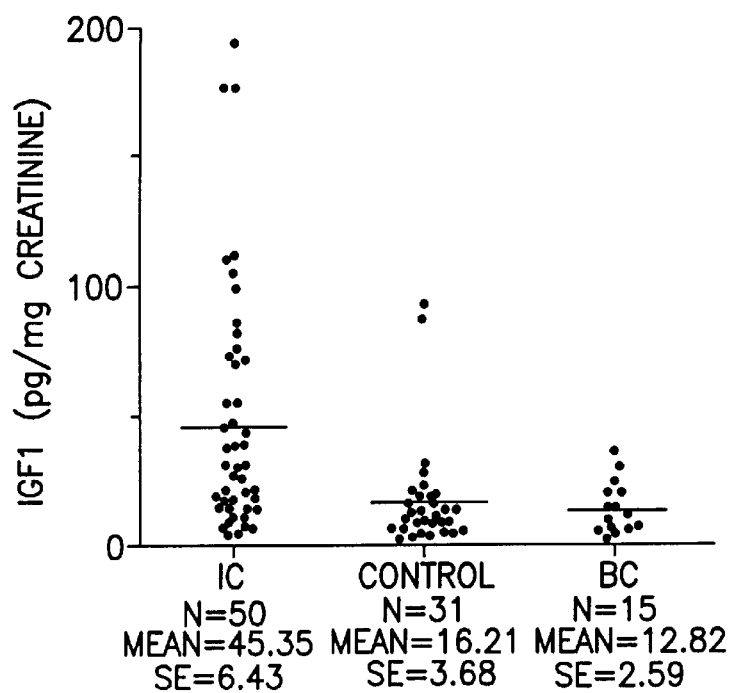

With respect to FIG. 3, quantities of immunoreactive IGF1 in the urine were measured because of the recognized importance of both IGF1 and IGF2 for bladder epithelial cell proliferation in vitro. A significant increase in urine IGF1 levels was evident in IC patients ($24.70\pm1.83$ pg/ml) as compared to asymptomatic controls ($12.11\pm1.08$ pg/ml, $p<0.001$) or specimens from bacterial cystitis patients ($14.97\pm3.58$ pg/ml, $p=0.01$) (see FIG. 3A). This finding was similarly true if the amount of urine IGF1 was expressed per milligram of urine creatinine ($p<0.001$ and $p=0.001$, respectively) (see FIG. 3B).

Figure 4A:
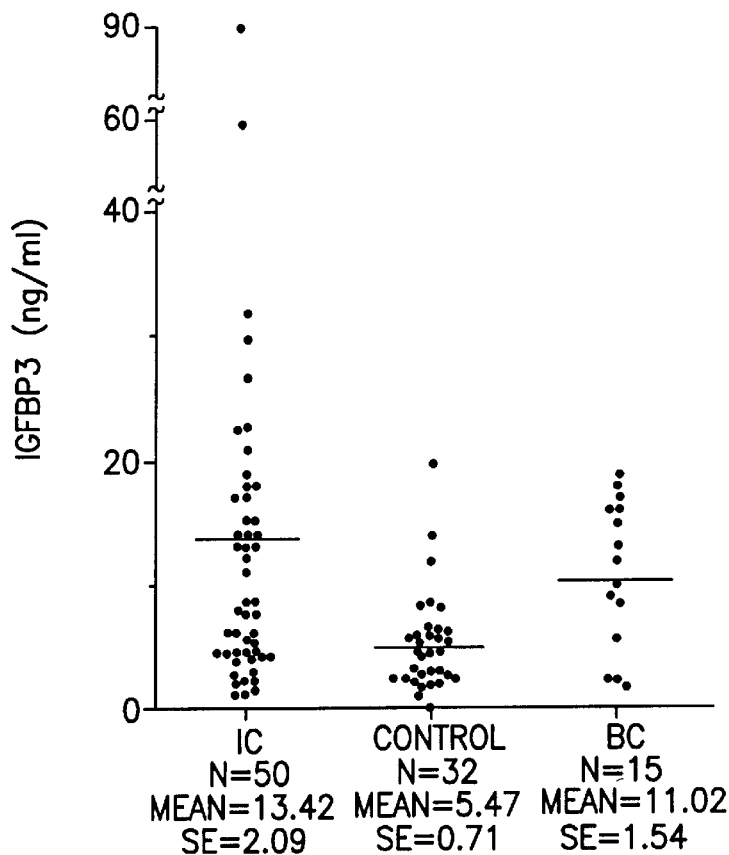
FIGS. 4A–4B: Depicts concentrations of IGFBP-3 in urine specimens from women with IC, asymptomatic control women without bladder disease, and women with acute, self-limited bladder epithelial damage from bacterial cystitis.
Figure 4B:
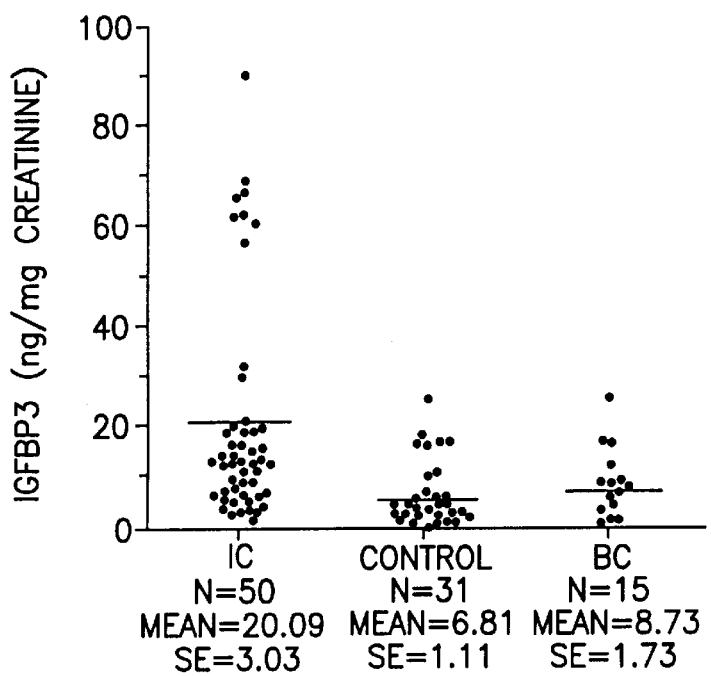

With respect to FIG. 4, the activity of the IGF's is modified by IGFBP's. IGFBP's or their peptides (generated by specific proteases) can have their own direct stimulatory or inhibitory effects on epithelial cells via IGFBP receptors. We chose to measure IGFBP3 as one of the predominant IGFBP's in urine. Our studies indicated that the concentration of IGFBP3 was significantly higher in the urine of IC patients ($13.42\pm2.09$ ng/ml) as compared to asymptomatic controls ($5.47\pm0.71$ ng/ml, $p=0.001$) (see FIG. 4A). This finding was also true when data were expressed per milligram of urine creatinine ($20.09\pm3.03$ ng/ml vs. $6.81\pm1.11$ ng/ml, $p<0.001$) (see FIG. 4B). However, the difference in concentration of urine IGFBP3 between IC and bacterial cystitis patients did not achieve statistical significance ($13.42\pm2.09$ ng/ml vs. $11.02\pm1.54$ ng/ml, $p=0.55$) (see FIG. 4A). When expressed per mg of urine creatinine, the difference was statistically significant ($20.09\pm3.03$ ng/ml for IC patients vs. $8.73\pm1.73$ ng/ml for bacterial cystitis patients, $p=0.004$) (see FIG. 4B). The ratio of IGF1 to IGFBP3 was also calculated for IC patients and their controls. Although there was a trend toward a lower ratio in the IC patients' urine than in urine from asymptomatic controls, the difference in IGF1:IGFBP3 between the two groups did not reach statistical significance ($p=0.09$).

Figure 11A:
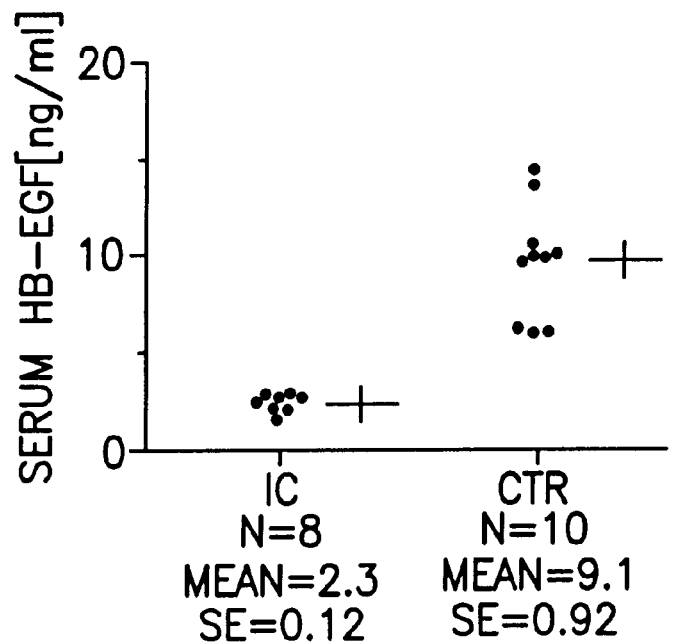
FIGS. 11A–B: Depicts serum growth factor levels (HB-EGF and EGF) in IC patients and controls by ELISA.
Figure 11B:
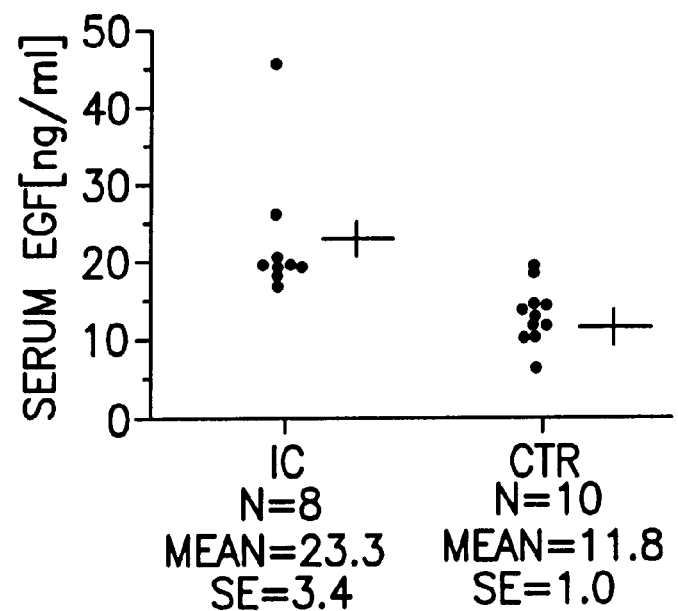

Regarding FIGS. 11A and 11B, HB-EGF is thought to generally function as an autocrine, paracrine or juxtacrine growth factor, being produced by, or nearby, the cells which it stimulates. There are no published data on serum levels of HB-EGF. However, in order to determine whether the APF and growth factor abnormalities identified in the urine of IC patients were confined to the urinary tract, serum levels of HB-EGF in 89 IC patients and 10 asymptomatic controls were determined by ELISA. The data suggest that circulating HB-EGF levels are also significantly lower in IC patients than controls (FIG. 11A), indicating that IC may be a urinary tract manifestation of a generalized physiologic process. In comparison, EGF levels were higher in the serum of IC patients than controls (FIG. 11B). These data indicate that differences in these epithelial cell growth factor levels between IC patients and controls are not confined to the urinary tract. [Each data point represents a mean of the duplicate determinations. Vertical lines indicate standard error of the group mean ($p<0.05$)]

C. Discussion

The limited data that exist for bladder epithelial cell growth suggest that replication and differentiation are influenced by growth factors and regulatory proteins of growth factors. Of greatest interest as potential stimulators of bladder epithelial cell replication is HB-EGF, which is produced by bladder epithelial cells and can stimulate their growth in vitro[26,27]. HB-EGF is produced by both kidney and bladder epithelial cells[20,24,26]. HB-EGF is capable of autocrine and/or paracrine activity, having effects on the cell of origin as well as neighboring or distant cells within the urinary tract. HB-EGF was specifically decreased in the urine of IC patients as compared to both asymptomatic controls and patients with bacterial cystitis. This decrease could also occur as a result of other inherent abnormalities in IC that secondarily affect HB-EGF synthesis which may or may not be causally related to the disease process. Because HB-EGF is produced by bladder epithelial cells, it is conceivable that urine levels of this growth factor may be secondarily decreased as a result of thinning and denudation of epithelial cells as seen in IC. Furthermore, epithelial cell surface glycosaminoglycans, which are commonly decreased in IC[6], can influence binding to the HB-EGF receptor[37] and could therefore influence HB-EGF production secondarily. However, HB-EGF has been shown to be important for replication of a variety of epithelial cells including hepatocytes, keratinocytes, gastric epithelial cells, and uterine epithelial cells, and is known to stimulate bladder epithelial replication in vitro[18-20,26,27]; it is therefore possible that decreased synthesis of HB-EGF by epithelial or other bladder cells contributes to the pathogenesis of IC by impairing normal bladder epithelial regeneration.

Part II. The Effect of APF on the Production of HB-EGF and Other Growth Factors

A. Materials and Methods

Patients and Urine Specimens:

The patients were screened and selected according to the protocol discussed in the preceding section. Likewise, the urine specimens were collected and maintained according to the protocol discussed in the preceding section.

APF Purification

APF was purified to homogeneity from the urine of 8 IC patients by sequential purification involving size-exclusion chromatography, ion exchange chromatography, hydrophobic interaction chromatography, and reversed-phase HPLC.

Cell Cultures:

Primary normal adult human bladder epithelial (HBE) cells were seeded onto 96 well tissue culture plates at a concentration of $10^4$ cells/well and grown overnight in Eagle's minimal essential medium (MEM) containing 10% heat inactivated FBS, 1% antibiotic/anti-mycotic solution, 1% glutamine, and 1.0 mg/ml insulin. All cells were cultured at 37 degrees C. in a 5% $CO_2$ atmosphere. On the second day, the culture medium was removed and replaced with serum-free MEM containing 1% antibiotic/antimycotic solution, 1% glutamine, and 1.0 mg/ml insulin.

On the third day, cell medium was replaced by serum free MEM containing 0.1 ng/$10^6$ cells HPLC purified APF (or mock APF) for 48 hours, with 10 $\mu$Ci $^{35}$S-methionine added for the final 12 hours of incubation. Spent culture medium was harvested and growth factor levels determined by ELISA (FIGS. 5A–5D). Cells were also harvested and $^{35}$S-methionine incorporation into TCA-precipitable contents determined for normalization to total cell protein. Data are mean values of triplicate specimens. Vertical bars show the standard error of the mean.

HB-EGF mRNA determination:

Total cellular RNA was extracted from human bladder epithelial cells incubated with IC or control urine specimens (FIG. 9A) or HPLC-purified APF or mock purified APF (FIG. 9B), and an RNase protection assay performed using a human pro-HB-EGF cDNA (obtained from Scios, Inc) and T7 RNA polymerase (Ambion) to prepare $^{32}$P-labeled antisense RNA probes. β-actin probes prepared from plasmid provided by Ambion were used as an internal control.

B. Results

Figure 7A:
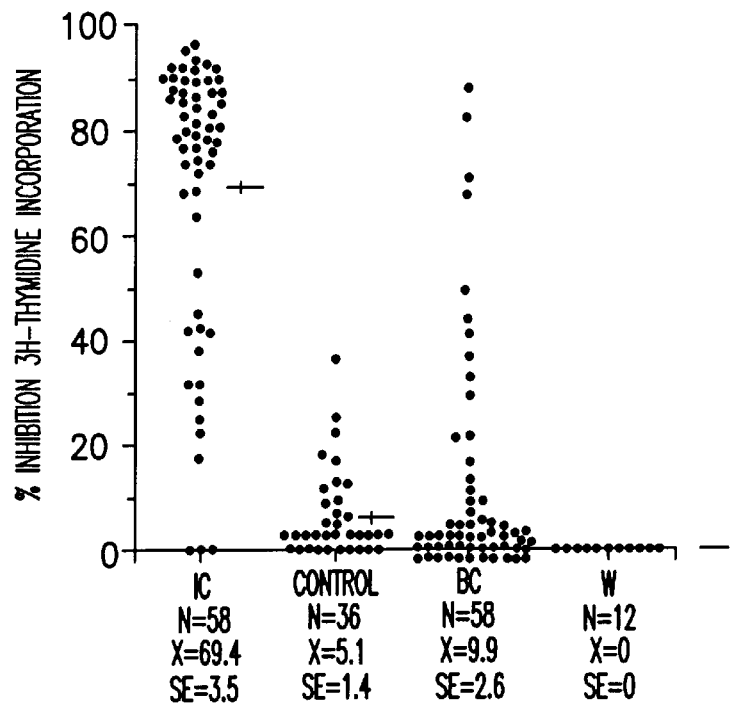
FIGS. 7A–7B.

Osmolality- and pH-corrected urine specimens from patients who fulfilled the NIDDK criteria for the diagnosis of IC were found to inhibit the proliferation of normal bladder epithelial cells in vitro significantly more often than urine specimens from asymptomatic controls, patients with acute bacterial cystitis, or patients with vulvovaginitis (FIG. 7A). This assay had optimal sensitivity and specificity values of 91.4% and 90.6%, respectively, for IC[38,39]. Data are expressed as the percent inhibition of 3H-thymidine incorporation in cells incubated for 48 hours with either IC urine specimens or control urine specimens diluted in serum-free cell culture medium compared with cells incubated with serum free medium alone. Each data point is the mean of 3–6 determinations. Horizontal bars indicate the mean value of the data points for each group. Vertical bars indicate the standard error of this mean.

Figure 7B:
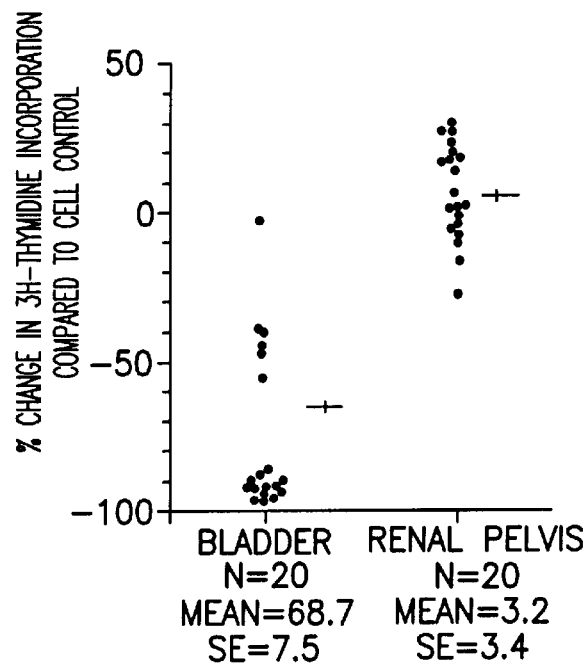

Catheterized urine specimens collected from the bladder of 20 female IC patients had antiproliferative activity significantly more often than specimens collected from the renal pelvis of the same patients (FIG. 7B), suggesting that the APF may be produced within the urinary tract. Data are expressed as the percent inhibition of 3H-thymidine incorporation in cells incubated for 48 hours with either IC urine specimens or control urine specimens diluted in serum-free cell culture medium compared with cells incubated with serum free medium alone. Each data point is the mean of 3–6 determinations. Horizontal bars indicate the mean value of the data points for each group. Vertical bars indicate the standard error of this mean.

It was determined that primary bladder epithelial cells from IC patients produced the factor in vitro. Cells grown from the bladder biopsies of 8 IC patients (5 female and 3 male) all produced an antiproliferative factor that inhibited the proliferation of normal bladder epithelial cells (mean % change in 3H-thymidine incorporation −88±12); in comparison, spent cell medium from bladder epithelial cells grown from 3 control patients stimulated the growth of other normal epithelial cells (+102±34%), providing additional evidence that this factor may be specific for IC.

The APF peptide was isolated from the urine of 8 IC patients as well as the culture medium of bladder epithelial cell explants from 5 IC patients, and determined to have a molecular mass of approximately 2.5 kDa by mass spectrometry (FIG. 8). In comparison, identical fractions purified from the urine of 3 controls had no protein isolated. MALDI-TOF mass spectrometric analysis was performed on PerSeptive Biosystems (Framinghham, Mass.) Voyager. Mass calibration was done using as standards angiotensin I, ACTH (Clip 1–17), ACTH (clip 18–39), ACTH (clip 7–38), and bovine insulin (PE Biosystems, Poster City, Calif.). α-cyano-4-hydroxcinnamic acid (Aldrich Chemical Co., Milwaukee, Wis.) at 10 mg/ml in 30% acetonitrile/0.3% trifluoroacetic acid was used as matrix.

As described above and shown in FIGS. 5A–5D, we determined the levels of specific growth factors HB-EGF, EGF, and IGF1 and growth factor binding protein, IGFBP3, produced by primary bladder epithelial cells in the presence of HPLC-purified APF. The quantity of immunoreactive HB-EGF produced in the presence of APF was markedly decreased as compared to that produced by mock APF controls and as compared to levels of other growth factors tested. As shown in FIG. 5A, the mean level of HB-EGF produced in the presence of HPLC-purified APF (0.2+0.1 ng/ml) was significantly lower than the mean level produced by cells in the presence of mock control (0.9+0.3 ng/ml). In comparison, production of EGF, IGF1, and IGFBP3 was increased in the presence of APF and mock APF (FIGS. 5B, 5C, and 5D respectively). The data was normalized to generalized protein synthesis, as determined by 35S-methionine incorporation. Specifically, the mean level of EGF produced in the presence of APF (2.3+0.5 ng/ml) was significantly higher than the mean level produced by cells in the presence of mock control (0.9+0.35 nglml) (note FIG.

5B). Likewise, the mean level of IGF1 produced in the presence of APF (21.7+4.2 pg/ml) was significantly higher than the mean level produced by cells in the presence of mock control (7.8+2.3 pg/ml) (note FIG. 5C), and the mean levels of IGFBP3 produced by cells in the presence of APF (3.4+0.5 ng/ml) was significantly higher than the mean level produced by cells in the presence of mock control (1.62+ 0.7).

Figure 9A:
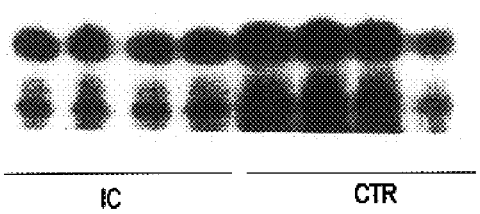
FIGS. 9A–B: Depicts the HB-EGF mRNA levels in cells exposed to APF. Total cellular RNA extracted from human bladder epithelial cells were incubated with IC or control urine specimens.
Figure 9B:
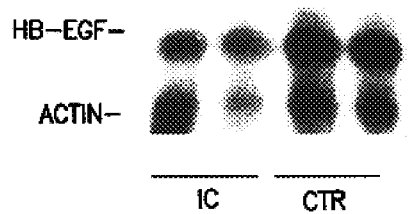

To further understand the mechanism by which the APF inhibits HB-EGF production is currently being investigated, we tested the effect of APF on HB-EGF mRNA production. Our data indicate that normal bladder epithelial cells exposed to urine specimens from IC patients do not have any decrease in proHB-EGF mRNA as compared to cells exposed to urine from control patients (FIG. 9A). In fact, in 4 of 5 experiments, the levels of proHBF-EGF mRNA were 20–25% increased as a result of APF exposure. HPLC-purified APF similarly did not affect HB-EGF mRNA levels (FIG. 9B). These data indicate that the decrease in HB-EGF production occurs post-transcriptionally.

C. Discussion

Human bladder epithelial cells are known to produce HB-EGF[26]. Since IC is histologically characterized by epithelial abnormalities and because the mucosal defects present in IC result in exposure of basal undifferentiated cells and their growth factor receptors to urine growth factors, we reasoned that abnormally low levels of urinary growth factors, such as HB-EGF, that stimulate bladder epithelial cell proliferation could adversely affect bladder epithelial wound repair and be part of the etiology of IC.

Primary bladder epithelial cells exposed to HPLC-purified APF produced decreased amounts of HB-EGF and increased amounts of EGF, IGF1, and IGFBP3 into the cell medium, as compared to cells incubated with mock APF purified from the urine of controls or serum-free medium alone (FIGS. 5A–5D). These findings indicate that the APF by itself can regulate the production of at least 3 growth factors and 1 growth factor binding protein by bladder epithelial cells, duplicating changes in these growth factor levels found in IC urine specimens (data not shown).

Our findings indicate that complex changes in the levels of urine growth factors are associated with IC, including significant and specific decreases in HB-EGF levels in the urine of IC patients (see co-pending application Ser. No. 60/051,458). The data herein supports our theory that inhibition of epithelial cell proliferation in vitro in the presence of IC urine and under conditions of serum starvation is related to a dysregulation of HB-EGF production caused by the APF in IC urine. Furthermore, our experimental data shows that the in vitro production of HB-EGF by bladder epithelial cells is specifically decreased in the presence of the APF, which is known to inhibit bladder cell proliferation, whereas production of other factors such as EGF, IGF1 and IGFBP3 is increased. These findings suggest that bladder epithelial cell synthesis or catabolism of specific autocrine growth factors may be regulated by the APF. This data supports our theory that there is a regulatory interaction between HB-EGF and the APF found in IC. Therefore, local administration of HB-EGF, either from exogenous or endogenous sources, may be used as an effective therapeutic for the treatment of IC, to counteract the production suppression caused by the APF.

Part III. Assaying the Inhibition of Anti-Proliferative Activity

A. Materials and Methods

Patients and Urine Specimens:

The patients were screened and selected according to the protocol discussed in the preceding section. Likewise, the urine specimens were collected and maintained according to the protocol discussed in the preceding section.

Cell Cultures:

Primary normal adult human bladder epithelial (HBE) cells were cultured by the method described above in Part II. On the third day of incubation, cell medium was replaced by serum free MEM containing the less than 3 kDa fraction (i.e, containing the APF) of urine specimens from IC patients or controls (i.e., that part containing the anti-proliferative factor or APF described in related application Ser. No. 08/944, 202), or HPLC-purified APF or its mock control along with varying concentrations of recombinant HB-EGF (0–100 ng/ml), EGF (0–100 ng/ml), or IGF-1 (0–300 pg/ml) [all from R & D Systems, Minneapolis, Minn.] diluted in phosphate buffered saline (1:1:1). Urine was prepared by the method described above in Part II and HPLC purified APF was prepared as described above. Following an additional 48 hours of incubation at 37 degrees C. in a 5% $CO_2$ atmosphere, cell proliferation was assessed by $^3$H-thymidine incorporation according to the published methods[38].

B. Results

Figure 6A:
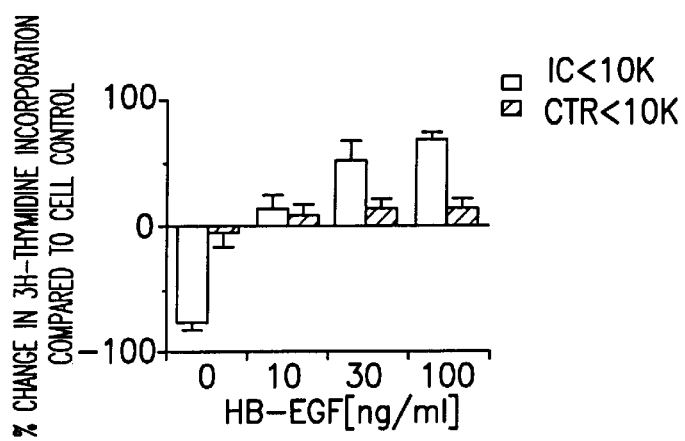
FIGS. 6A–C: Depicts the inhibition of APF activity (i.e., the stimulation of bladder epithelial cell proliferation) by recombinant human growth factors [HB-EGF, EGF and IGF1].
Figure 6B:
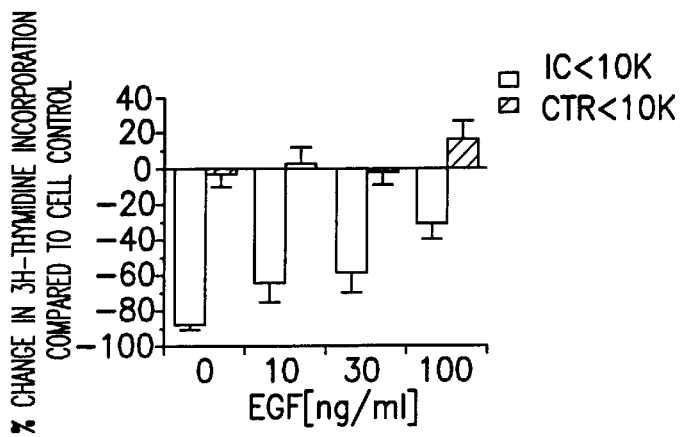
Figure 6C:
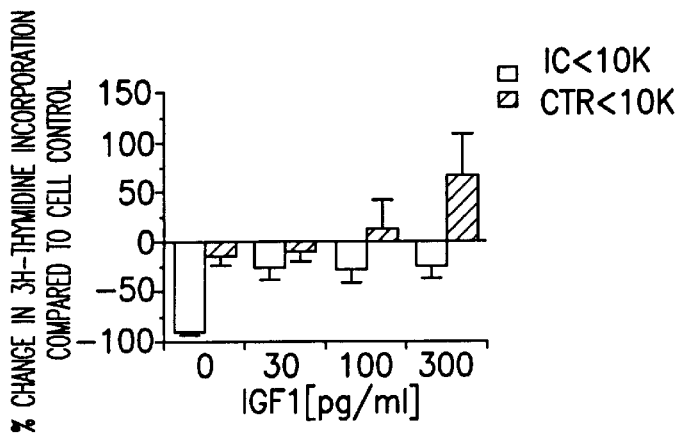

Normal human bladder epithelial cells were exposed simultaneously to recombinant human growth factors (HB-EGF, EGF, or IGF1) and low molecular weight fractions from IC patients or control urine specimens. Cell proliferation was determined 48 hours later by 3H-thymidine incorporation (FIGS. 6A–6C). Bar values indicate the mean of 5–8 determinations. Vertical lines indicate the standard error of the mean.

The simultaneous exposure of normal human bladder epithelial cells to rhHB-EGF and low molecular weight fractions of urine from IC patients or controls resulted in inhibition of APF antiproliferative activity (FIG. 6A), suggesting that the APF activity is mediated by downregulation of HB-EGF production. This dose-dependent effect was evident at both physiologic (10 ng/ml) and supraphysiologic HB-EGF concentrations. In fact, at high concentrations of rhHB-EGF the proliferation or cells exposed to urine from IC patients was stimulated, more than that of cells exposed to control urines, possibly indicating the increased presence of other low molecular weight urine growth factors. In comparison, even supraphysiologic concentrations of recombinant EGF or IGF1 (R&D Systems) (12 and 25 fold greater than normal, 2 and 5 fold greater than the highest measured in IC urine specimens, respectively) were unable to completely inhibit APF activity (FIGS. 6B and C).

These data indicate that bladder epithelial cells from IC patients can proliferate in response to exogenous HB-EGF, indicating that they are likely to have functional HER-1 receptors, and that the inhibition of bladder cell epithelial cell proliferation in vitro caused by a factor that is specific for IC urine specimens can be blocked by the addition of a single growth factor (HB-EGF) at concentrations similar to those measured in urine specimens from normal controls. This suggests that rHB-EGF or agents that stimulate its production or mimic its activity may be useful for the treatment of IC, a bladder disorder characterized by chronically damaged epithelium.

Figure 10A:
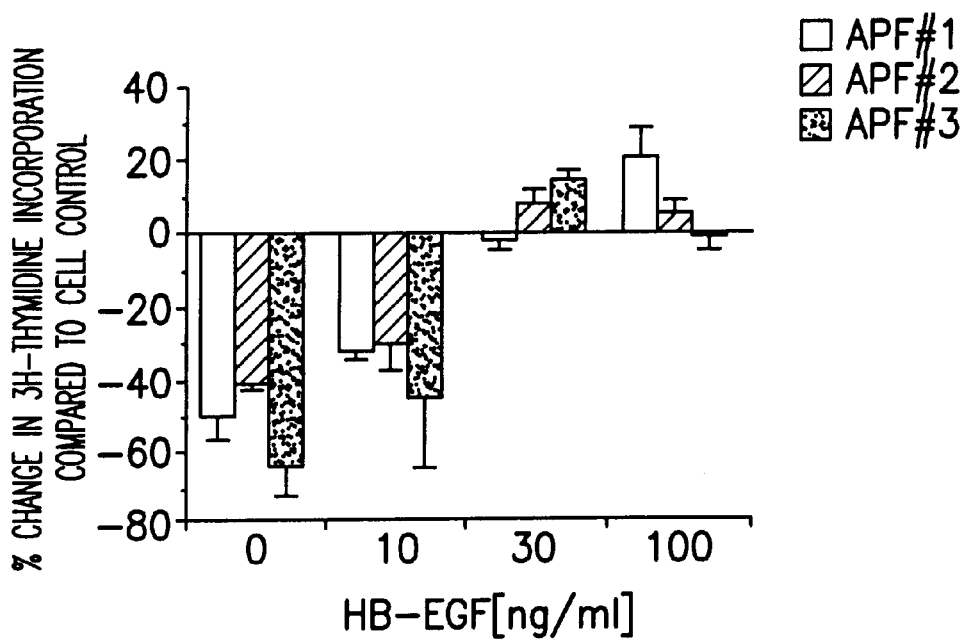
FIGS. 10A–B: Depicts inhibition of HPLC-purified APF activity by rhHB-EGF.
Figure 10B:
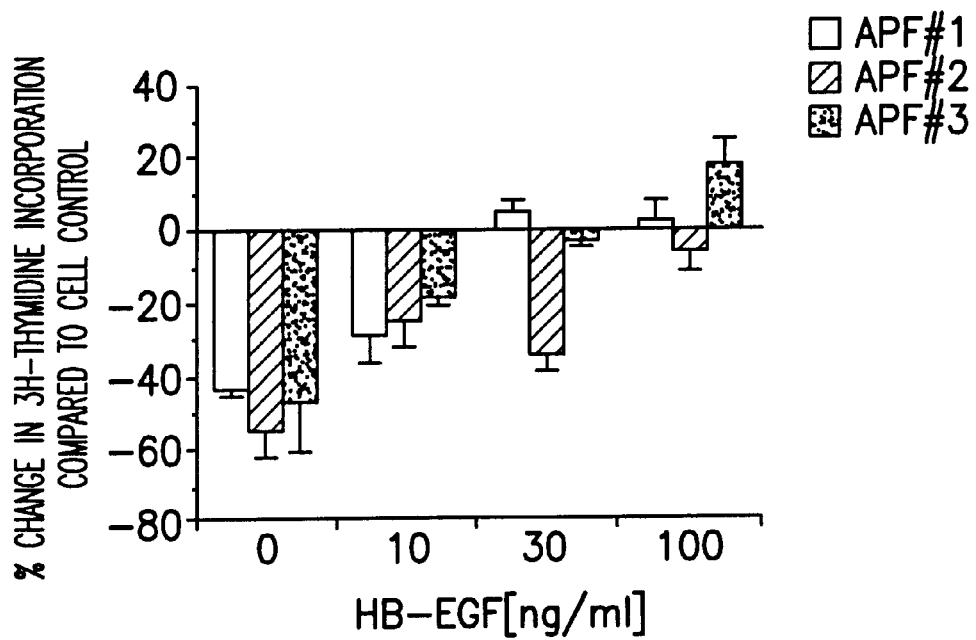

As shown in FIGS. 10A and B, primary human bladder epithelial cells were exposed simultaneously to recombinant human HB-EGF and 10 pg/10$^7$ cells HPLC-purified APF. Cell proliferation was determined 48 hours later by 3H-thymidine incorporation. Bar values indicate the mean of triplicate determinations. Vertical lines indicate the standard of error of the mean. FIG. 10A shows cells grown from normal bladder tissue. FIG. 10B shows cells grown from IC patient biopsy specimens. The experiments using HPLC-purified APF confirm that recombinant human HB-EGF can inhibit APF's antiproliferative effects on cells from both IC patients and controls (FIG. 10).

C. Discussion

The data herein indicate that the inhibition of bladder epithelial cell proliferation caused by the APF from IC urine specimens can be blocked by the addition of recombinant HB-EGF to the cell medium. HB-EGF appears to act as an antagonist for the APF. Therefore, HB-EGF may be used as an effective therapeutic for the treatment of IC. Additionally, as we have demonstrated that HB-EGF is capable of inhibiting the anti-proliferative activity, it stands to reason that it could provide a reliably effective therapy for other disorders associated with inhibited epithelial cell proliferation, particularly bladder epithelial cell proliferation. The criticality lies in the ability of HB-EGF to locally combat the anti-proliferative activity. The growth factor can be exogenously administered to injured epithelial cells in a form suitable to provide the desired stimulation of cell replication. The form may be suitable for local or topical application, such as a liquid, a cream, an ointment, a suppository, or a gel that may be superficially applied to the tissues. Alternatively, the form may be suitable for systemic administration, such as oral or parenteral formulations. The administration may be in the form of discrete doses or in a form capable of continuous delivery.

The criticality lies in the achievement of the stimulation of cell replication by HB-EGF. This stimulation is not limited to exogenous administration of HB-EGF to the epithelial cells. Rather, it may be achieved by administering agents that stimulate endogenous HB-EGF production, agents that inhibit HB-EGF degradation, agents that stimulate HB-EGF receptor binding or receptor activity in response to HB-EGF.

Specifically, the present invention should not be interpreted to apply to HB-EGF but also to active fragments of this growth factor, as well as to functional derivatives, agonists and antagonists, and metabolic breakdown products of this growth factor. The invention especially concerns agents which are capable of inhibiting this growth factor.

A "functional derivative" of HB-EGF is a compound which possesses a biological activity (either functional or structural) that is substantially similar to a biological activity of HB-EGF, for example inhibit the antiproliferative activity of the APF in bladder cells. The term "functional derivatives" is intended to include the "fragments," "variants," "analogues," or "chemical derivatives" of a molecule. A "fragment" of a molecule such as HB-EGF, is meant to refer to any polypeptide subset of the molecule. A "variant" of a molecule such as HB-EGF is meant to refer to a molecule substantially similar in structure and function to either the entire molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules is not found in the other, or if the sequence of amino acid residues is not identical. An "analogue" or agent which mimics the function of a molecule such as HB-EGF is meant to refer to a molecule substantially similar in function but not in structure to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980). Procedures for coupling such moieties to a molecule are well known in the art.

Analogues of HB-EGF or agents which mimic the function of HB-EGF can be used as therapeutic molecules as well, inhibiting anti-proliferative activity or function of the APF. HB-EGF or HB-EGF analogues can provide reliably effective therapy for other disorders associated with inhibited epithelial cell proliferation, particularly bladder epithelial cell proliferation. Analogues of HB-EGF may further comprise immunoglobulins (such as, for example, monoclonal or polyclonal antibody, or active fragments of such antibody). The analogues of the present invention may also include non-immunoglobulin compounds (such as polypeptides, organic compounds, etc.)

An analogue of HB-EGF may further comprise a polyclonal antibody capable of binding to APF. Such can be prepared by immunizing a mammal with a preparation of APF or functional derivative of APF. Methods for accomplishing such immunizations are well known in the art. Monoclonal antibodies (or fragments thereof) can also be employed to assay for the presence (or amount) or APF in a particular biological sample. Such antibodies can be produced by immunizing splenocytes with activated APF (by modifying the procedures of Kohler et al. (*Nature* 256:495 (1975); *Eur. J. Immunol.* 6:511 (1976); *Euro J. Immunol.* 6:292 (1976)).

In addition to the above methods, antibodies capable of binding to the receptor for HB-EGF may be produced in a two step procedure through the use of anti-idiotypic antibodies. Such a method makes use of the fact that antibodies are themselves antigens, and that, therefore, it is possible to obtain an antibody which binds to a second antibody. In accordance with this method, antibodies capable of binding to HB-EGF are used to immunize an animal. The splenocytes of such an animal are then used to produce hybridoma cells, and the hybridoma cells are screened to identify clones which produce antibody whose ability to bind to anti-HB-EGF antibodies can be specifically blocked by HB-EGF. Such antibodies comprise anti-idiotypic antibodies to the anti-HB-EGF antibody. Such antibodies can be used to immunize an animal, and thereby induce the formation of antibodies capable of binding to HB-EGF. Anti-idiotypic antibodies, or other agents which mimic HB-EGF, could be used as a therapeutic agent in a manner similar to that of HB-EGF itself.

In addition to providing HB-EGF (or a functional derivative of APF) to a subject, the efficacy of HB-EGF in a subject can be increased by the administration of an agonist of HB-EGF to a subject. The invention additionally pertains to such agonists of HB-EGF. An agonist of HB-EGF is any compound which is capable of increasing the efficacy of a function of HB-EGF. Examples of such agonists include an agent which promotes the synthesis of HB-EGF by the subject, etc. Agonists can be used to induce HB-EGF in normal cells for testing drugs and treatments and for diagnostic purposes. Additionally, anti-idiotypic antibodies, or analogues of HB-EGF, or agents which mimic HB-EGF activity, or a combination of any of the above can be provided to a subject in need of such treatment.

HB-EGF may be obtained synthetically, through the use of recombinant DNA technology, or by proteolysis. The therapeutic advantages of such agents may be augmented through the combined administration of several agents. The scope of the present invention is further intended to include functional derivatives of HB-EGF which lack one, two, or more amino acid residues, or which contain altered amino acid residues, so long as such derivatives exhibit the capacity to influence cell proliferation.

The examples provided herein are for illustrative purposes only, and are in no way intended to limit the scope of the present invention. While the invention has been described in detail, and with reference to specific embodiments thereof, it will be apparent to one with ordinary skill in the art that various changes and modifications can be made therein without departing from the spirit and scope thereof.

All references cited herein are incorporated by reference in their entirety.

References

1. Hanno, P. M., Staskin, D. R., Krane, R. J., and Wein, A. J., eds. *Interstitial Cystitis*. London: Springer-Verlag, 1990.
2. Held, P. J., Hanno, P. M., Wein, A. J., Pauly, M. V., and Cann, M. A.: *Epidemiology of interstitial cystitis. 2. In: Interstitial Cystitis*. Edited by P. M. Hanno, D. R. Staskin, R. J. Krane, and A. J. Wein. London: Springer-Verlag, pp. 29–48, 1990.
3. Johansson, S. L. and Fall, M. *Clinical features and spectrum of light microscopic changes in interstitial cystitis*. J. Urol., 143: 1118, 1990.
4. Oravisto, K. J., Alfthan, O. S. and Jokinen, E. J. *Interstitial cystitis: Clinical and immunological findings*. Scand. J. Urol. Nephrol., 4: 37, 1970.
5. Skoluda, D., Wegner, K. and E. -M. Lemmel. *Kritische Bemerkungen zur Immunopathogenese der interstitiellen Cystitis*. Urologe, 13:15, 1974.
6. Parsons, C. L., Lilly, J. D. and Stein, P. *Epithelial dysfunction in nonbacterial cystitis (interstitial cystitis)*. J. Urol., 145: 732, 1991.
7. Smith, B. H. and Dehner, L. P. *Chronic ulcerating interstitial cystitis (Hunner's ulcer)*, Arch. Path., 93: 76, 1972.
8. Fowler, J., Jr, Lynes, W. L., Lau, J. L. T., Ghosh, L., and Mounzer, A. *Interstitial cystitis is associated with intraurothelial Tamm-Horsfall protein*. J. Urol., 140: 1385, 1988.
9. Liebert, M., Wedemeyer, G., Stein, J. A., Washington, R., Jr., Faerber, G., Flint, A. and Grossman, H. B. *Evidence for urothelial cell activation in interstitial cystitis*. J. Urol., 149: 470, 1993.
10. deBoer, W. I., Schuller, A. G. P., Vermey, M., and van der Kwast, T. H. *Expression of growth factors and receptors during specific phases in regenerating urothelium after acute injury in vivo*. Am. J. Pathol. 145: 1199, 1994.
11. Lynch, S. E., Colvin, R. B., and Antoniades, H. N. Growth factors in wound healing. *Single and synergistic effects on partial thickness porcine wounds*. J. Clin. Invest. 84: 640, 1989.
12. Mustoe, T. A., Pierce, G. F., Morishima, C., and Deuel, T. F. *Growth factor-induced acceleration of tissue repair through direct and inductive activities in a rabbit dermal ulcer model*. J. Clin. Invest. 87: 694, 1991.
13. Mellin, T. N., Mennie, R. J., Cashen, D. E., Ronan, J. J., Capparella, J., James, M. L., Disalvo, J., Frank, J., Linemeyer, D., Giminez-Gallego, G., and Thomas, K. A. *Acidic fibroblast growth factor accelerates dermal wound healing*. Growth Factors 7: 1, 1992.
14. Antoniades, H. N., Galanopoulos, T., Neville-Golden, J., Kiritsky, C. P., and Lynch, S. E. *Expression of growth factor and receptor mRNAs in skin epithelial cells following acute cutaneous injury*. Am. J. Pathol. 142: 1099, 1993.
15. Werner, S., Peters, K. G., Longaker, M. T., Fuller-Pace, F., Banda, M. J., and Williams, L. T. *Large induction of keratinocyte growth factor expression in the dermis during wound healing*. Proc. Natl. Acad. Sci. USA 89: 6896, 1992.
16. Nusrat, A., Parkos, C. A., Bacarra, A. E., Godowski, P. J., Delp-Archer, C., Rosen, E. M., and Madara, J. L. *Hepatocyte growth factor/scatter factor effects on epithelia*. J. Clin. Invest. 93: 2056, 1994.
17. Behrens, M. T., Corbin, A. L., and Hise, M. K. *Epidermal growth factor receptor regulation in rat kidney: two models of renal growth*. Am. J. Physiol. 257: F1059, 1989.
18. McCarthy, D. W., Downing, M. T., Brigstock, D. R., Luquette, M. H., Brown, K. D., Abad, M. S., and Besner, G. E. *Production of heparin-binding epidermal growth factor-like growth factor (HB-EGF) at sites of thermal injury in pediatric patients*. J. Invest. Dermatol. 106: 49, 1996.
19. Marikovsky, M., Breuing, K., Liu, P. Y., Eriksson, E., Higashiyama, S., Farber, P., Abraham, J., and Klagsbrun, M. *Appearance of heparin-binding EGF-like growth factor in wound fluid as a response to injury*. Proc. Natl. Acad. Sci USA 90: 3889, 1993.
20. Homma, T., Sakai, M., Cheng, H. F., Yasuda, T., Coffey, R. J., Jr., and Harris, R. C. *Induction of heparin-binding epidermal growth factor-like growth factor mRNA in rat kidney after acute injury*. J. Clin. Invest. 96: 1018, 1995.
21. de Boer, W. I., Rebel, J. M. J., Venney, M., de Jong, A. A. W., and van der Kwast, T. H. *Characterization of distinct functions for growth factors in murine transitional epithelial cells in primary organotypic culture*. Exp. Cell Res. 214: 510, 1994.
22. Jorgensen, P. E., Hilchey, S. D., Nexo, E., Poulsen, S. S., and Quilley, C. P. *Urinary epidermal growth factor is excreted from the rat isolated perfused kidney in the absence of plasma*. J. Endocrinol. 139: 227, 1993.
23. Southgate, J., Hutton, A. R., Thomas, D. F. M., and Trejdosiewicz, L. K. *Normal human urothelial cells in vitro: proliferation and induction of stratification*. Lab. Invest. 71: 583, 1994.
24. Chin, E. and Bondy, C. *Insulin-like growth factor system gene expression in the human kidney*. J. Clin. Endocrinol. Metab. 75: 962, 1992.
25. Jones, J. I. and Clemmons, D. R. *Insulin-like growth factors and their binding proteins: biological actions*. Endocrine Rev. 16: 3, 1995.
26. Freeman, M. R., Schneck, F. X., Soker, S., Raab, C., Tobin, M., Yoo, J., Klagsbrun, M., and Atala, A. *Human*

27. *urothelial cells secrete and are regulated by heparin-binding epidermal growth factor-like growth factor (HB-EGF)*. Proc. Am. Urol. Assoc. 153: 316A, 1995.
27. Tobin, M. S., Freeman, M. R., Schneck, F. X., Klagsbrun, M., and Atala, A. *Growth factor biology of human urothelial cells grown under serum-free conditions*. Proc. Am. Urol. Assoc. 153: 406A, 1995.
28. Division of Kidney, Urologic, and Hematologic Diseases (DKUHD) of the National Institute of Diabetes and Digestive and Kidney Diseases (NIDDK). *Diagnostic criteria for research studies (interstitial cystitis)*. Am. J. Kidney Dis. 13:353, 1989.
29. Third International Symposium on Insulin-like Growth Factors. *Valid measurements of total IGF concentrations in biological fluids*. Endocrinology 136: 816, 1995.
30. Schirmeister, J., Willman, H., and Kiefer, H. *Plasmakreatinin alf grober Indikator der Nierenfunktion*. Dtsch. Med. Wschr. 89: 1018, 1964.
31. Quattrin, T., Albini, C. H., Mills, B. J., and MacGillivray, M. *Comparison of urinary growth hormone and IGF-1 excretion in small- and appropriate-for-gestational-age infants and healthy children*. Pediatr. Res. 28: 209, 1990.
32. Dreyer, M., Matthaei, S., Kuhnau, J., and Rudiger, H. W. *Prolonged plasma half-life of insulin in patients with a genetic defect of high affinity binding sites*. Horm. Metab. Res. 18: 247, 1986.
33. Nanjo, K., Kondo, M., Sanke, T., and Nishi, M. *Abnormal insulinemia*. Diabetes. Res. Clin. Pract. 24 Suppl: S135, 1994.
34. Moxham, C. M. and Malbon C. C. *Insulin action impaired by deficency of the G-protein subunit G ialpha2*. Nature 379: 840, 1996.
35. Weaver, J. U., Hitman, G. A., and Kopelman, P. G. *An association between a BclI restriction fragment length polymorphism of the glucocorticoid receptor locus and hyperinsulinaemia in obese women*. J. Mol. Endocrinol. 9: 295, 1992.
36. Matejka, G. L. and Jennische, E. *IGF-1 binding and IGF-1 mRNA expression in the post-ischemic regenerating rat kidney*. Kidney Int. 42: 1113, 1992.
37. Shishido, Y., Sharma, K. D., Higashiyama, S., Klagsbrun, M., Mekada, E. *Heparin-like molecules on the cell surface potentiate binding of diptheria toxin to the diphtheria toxin receptor/membrane-anchored heparin-binding epidermal growth factor-like growth factor*. J. Biol. Chem. 270: 29578, 1995.
38. Keay, S., Zhang, C. -O., Hise, M., Trifillis, A. L., Hebel, J. R., Jacobs, S. C., and Warren, J. W. *Decreased $^3$H-thymidine incorporation by human bladder epithelial cells following exposure to urine from interstitial cystitis patients*. J. Urol. 156: 2073, 1996.
39. Keay, S., Zhang, C. -O, Hise, M., Hebel, J. R., Jacobs, Gordon, D., Whitmore, K., Bodison, S., Gordon, N., and Warren, J. W. *A diagnostic in vitro assay for Interstitial Cystitis*. Urology 52: 974, 1998.

What is claimed:

1. A method for enhancing bladder epithelial cell proliferation in a subject in need thereof, said method comprising administering to the subject heparin-binding epidermal growth factor-like growth factor, in an amount effective to enhance bladder epithelial cell proliferation.

2. The method of claim 1 wherein the subject has a condition which comprises interstitial cystitis.

3. The method of claim 2 wherein the heparin-binding epidermal growth factor-like growth factor comprises recombinant heparin-binding epidermal growth factor-like growth factor.

4. The method of claim 1 wherein the heparin-binding epidermal growth factor-like growth factor comprises recombinant heparin-binding epidermal growth factor-like growth factor.

5. The method of claim 1 wherein the step of administering step further comprises systemic administration.

6. The method of claim 5 wherein the systemic administration by a route selected from the group consisting of intravenous, subcutaneous, parenteral and oral.

7. The method of claim 1 wherein the step of administering further comprises local administration.

8. The method of claim 7 wherein the local administration comprises topical administration.

9. The method of claim 8 comprising administering the heparin-binding epidermal growth factor-like growth factor as a component of a pharmaceutical composition.

10. The method of claim 9 wherein the pharmaceutical composition has a form selected from the group consisting of liquids, creams, ointments, suppositories and gels.

11. The method of claim 7 wherein the local administration comprises intravesical administration.

12. The method of claim 11 comprising administering the heparin-binding epidermal growth factor-like growth factor as a component of a pharmaceutical composition.

13. The method of claim 12 wherein the pharmaceutical composition has a form selected from the group consisting of liquids, creams, ointments, suppositories and gels.

14. The method of claim 7 comprising administering the heparin-binding epidermal growth factor-like growth factor as a component of a pharmaceutical composition.

15. The method of claim 14 wherein the pharmaceutical composition has a form selected from the group consisting of liquids, creams, ointments, suppositories and gels.

16. The method of claim 1 wherein the step of administering further comprises exogenous administration.

17. The method of claim 1 wherein the step of administering further comprises endogenous administration.

18. A method for enhancing bladder epithelial cell proliferation in a subject with a condition comprising interstitial cystitis, said method comprising administering to the subject heparin-binding epidermal growth factor-like growth factor in an amount effective to enhance epithelial cell proliferation.

19. The method of claim 18 wherein the heparin-binding epidermal growth factor-like growth factor is administered as a component of a pharmaceutical composition.

20. A method for treating interstitial cystitis by enhancing bladder epithelial cell proliferation in a subject with a condition comprising interstitial cystitis, said method comprising administering to the subject heparin-binding epidermal growth factor-like growth factor in an amount effective to enhance bladder epithelial cell proliferation.

21. The method of claim 20 wherein the heparin-binding epidermal growth factor-like growth factor is administered as a component of a pharmaceutical composition.

22. A method for palliatively treating interstitial cystitis in a subject with a condition comprising interstitial cystitis, said method comprising administering to the subject heparin-binding epidermal growth factor-like growth factor in an amount effective to enhance bladder epithelial cell proliferation.

23. The method of claim 22 wherein the heparin-binding epidermal growth factor-like growth factor is administered as a component of a pharmaceutical composition.

* * * * *

UNITED STATES PATENT AND TRADEMARK OFFICE
CERTIFICATE OF CORRECTION

PATENT NO. : 6,232,289 B1
DATED : May 15, 2001
INVENTOR(S) : Keay et al.

It is certified that error appears in the above-identified patent and that said Letters Patent is hereby corrected as shown below:

Title page, Item [54], and Column 1, Line 2,
Change "CYTITIS" to -- CYSTITIS --

Column 10,
Line 67, change "nglml" to -- ng/ml --

Signed and Sealed this

Nineteenth Day of February, 2002

Attest:

JAMES E. ROGAN
*Attesting Officer*  *Director of the United States Patent and Trademark Office*